United States Patent [19]

Williams

[11] 4,119,510

[45] Oct. 10, 1978

[54] PHOTOCURABLE DIISOCYANATE COMPOSITIONS

[75] Inventor: Ralph P. Williams, Bartlesville, Okla.

[73] Assignee: Phillips Petroleum Company, Bartlesville, Okla.

[21] Appl. No.: 629,946

[22] Filed: Nov. 7, 1975

[51] Int. Cl.$^2$ .................... C08F 2/46; C08F 8/18
[52] U.S. Cl. .................... 204/159.23; 204/159.15; 204/159.18; 204/159.24; 260/553 R; 260/859 R; 560/147; 560/148; 560/205; 560/222; 427/54; 528/75; 528/44
[58] Field of Search .................... 204/159.23, 159.18; 427/54; 260/77.5 CR, 77.5 AP

[56] References Cited

U.S. PATENT DOCUMENTS

| | | | |
|---|---|---|---|
| 3,759,809 | 9/1973 | Carlick et al. | 204/159.23 |
| 3,862,920 | 1/1975 | Foster et al. | 260/77.5 CR X |
| 3,864,133 | 2/1975 | Hisamatsu et al. | 204/159.23 X |
| 3,896,014 | 7/1975 | Rosenberg | 204/159.23 |
| 3,908,039 | 9/1975 | Guthrie et al. | 427/54 |

*Primary Examiner*—Richard B. Turer

[57] ABSTRACT

A prepolymer for use in preparing photocurable compositions is prepared by reacting an aliphatic diisocyanate having terminal isocyano groups and at least one alkyl side chain with a hydroxy-, mercapto- or amino-containing olefinically unsaturated compound. This prepolymer is compounded with a photosensitizer and, optionally, a polymercaptan to prepare photocurable compositions.

14 Claims, No Drawings

PHOTOCURABLE DIISOCYANATE COMPOSITIONS

This invention relates to a photocurable liquid composition.

Photocurable printing inks, coatings and adhesives are known in the art. They have not, however, found wide commercial acceptance either because of the slowness with which they cure, because they can be difficult to formulate, because they use exotic and expensive materials or because the cured product is inferior to other readily available materials.

Accordingly, it is an object of this invention to provide a novel photocurable composition.

Other objects, aspects and advantages of this invention will be readily apparent to those skilled in the art from the reading of the following disclosure.

In accordance with the present invention there is provided a novel photocurable prepolymer formed by the reaction of (A) an aliphatic diisocyanate having terminal isocyano groups and at least one alkyl side chain and (B) a hydroxy-, mercapto- or amino-containing olefinically unsaturated compound.

The aliphatic diisocyanate (A) contains from 9 to 32 carbon atoms per molecule and is characterized by the formula:

$$OCN-(CHR)_x-CH((CH_2)_z CH_3)-(CHR)_y-NCO$$

wherein each R is individually selected from the group consisting of hydrogen and alkyl having from 1 to 6 carbon atoms; $x$ is an integer having a value of 2 to 16, $y$ is an integer having a value of 2 to 16, the sum of $(x+y)$ is from 5 to 23, and $z$ is an integer having a value of 0 to 5.

Suitable aliphatic diisocyanates include 3-methylhexane-1,6-diisocyanate, 3-ethyl-1,6-hexanediisocyanate, 5-methyl-1,9-nonanediisocyanate, 5-ethyl-1,10-decanediisocyanate, 10-hexyl-1,24-tetracosanediisocyanate, 2,3-dimethyl-1,6-hexanediisocyanate, 2,4-dimethyl-1,8-octanediisocyanate, 2,4,6-trimethyl-1,7-heptanediisocyanate, 2,3-dimethyl-5-ethyl-1,8-octanediisocyanate and 2-methyl-4,6,8,10-tetrapropyl-1,12-dodecanediisocyanate and mixtures thereof.

Other diisocyanates which may be desired for some applications but which are not commercially available can be readily prepared from the corresponding diamines, employing well-known procedures, such as by phosgenation of the diamine hydrochloride.

In a presently preferred embodiment, the diisocyanate disclosed above contains from 10 to 18 carbon atoms per molecule, more preferably from 11 to 14 carbon atoms.

The olefinically unsaturated compound (B) contains up to and including 12 carbon atoms per molecule and is characterized by the formula $$R^i-C(R^i)=C(R^i)-Y_m-(CR^i_2)_n-Z$$

wherein each $R^i$ is individually selected from the group consisting of hydrogen and alkyl having from 1 to 6 carbon atoms, $n$ is an integer having a value of 1 to 6, Y is selected from the group consisting of $$-\overset{O}{\underset{\|}{C}}-O-, \quad -\overset{O}{\underset{\|}{C}}-S-, \text{ and } -\overset{O}{\underset{\|}{C}}-\underset{R^{ii}}{N}-,$$

$m$ is an integer having a value of 0 or 1, $R^{ii}$ is selected from the group consisting of $R^i$ and alkenyl having from 1 to 6 carbon atoms, and Z is selected from the group consisting of —OH, —SH and —NHR$^{ii}$.

Examples of suitable olefinically unsaturated compounds in which $m$ is 0 include allyl alcohol, 3-buten-1-ol, 2-buten-1-ol, 3-hepten-1-ol, 5-hexen-1-ol, 7-octen-1-ol, 1-dodecen-6-ol, 3,4-dimethyl-3-penten-1-ol, allylamine, diallylamine, methylallylamine, hexyl-5-hexenylamine, allyl mercaptan, 2-buten-1-thiol, 2,4,6-trimethyl-7-octen-1-thiol, and the like and mixtures thereof.

Examples of suitable olefinically unsaturated compounds in which $m$ is 1 include hydroxymethyl acrylate, hydroxyethyl acrylate, 4-hydroxybutyl methacrylate, 2,3-dimethyl-4-hydroxybutyl 2,3-dimethyl-2-butenoate, N-methyl-N-(6-hydroxyhexyl) acrylamide, 2-aminoethyl methacrylate, hydroxymethyl thioacrylate, 2-mercaptoethyl acrylate and the like and mixtures thereof.

The above prepolymers are prepared by reacting the aliphatic diisocyanate (A) and the olefinically unsaturated compound (B) under conditions of time and temperature which will result in the desired photocurable prepolymer. In general, a reaction temperature in the approximate range of 0° to 120° C., preferably 20° to 60° C., and a reaction time in the approximate range of 1 minute to 24 hours, preferably 5 minutes to 1 hour, are sufficient to bring about the desired results. The reaction can be carried out in the presence or absence of oxygen or air. Water should be excluded from the reaction system.

The diisocyanate (A) and the olefinically unsaturated compound (B) are generally mixed in stoichiometric proportions, i.e., 2 moles of (B) per mole of (A). It may be desirable to use an excess of up to about 10 mole percent of the olefinically unsaturated compound (B).

When desired, a catalyst can be employed to promote the reaction of the diisocyanate (A) with the olefinically unsaturated compound (B). Typical catalysts are organotin compounds, such as dibutyltin dilaurate and stannous octoate. Such catalysts are employed in a reaction promoting amount, i.e., generally from 0.01 to 1 weight percent, based on the total weight of reactants, preferably 0.1 to 0.5 weight percent. The use of such catalysts is particularly advantageous for the reaction of an olefinically unsaturated alcohol with a diisocyanate.

The prepolymer reaction product of the diisocyanate and the olefinically unsaturated compound is ready for use at the end of the reaction period. If desired, any unreacted or excess material can be removed by any suitable means, such as by vacuum flashing.

In one embodiment of the present invention, the above-described prepolymer is compounded with a polymercaptan, a photosensitizer and, optionally, a promoter, and then cured.

The term "polymercaptan" as used herein and in the claims, refers to simple or complex organic compounds having an average of at least two pendant or terminal mercaptan groups (—SH) per molecule. Such polymercaptans can generally be represented by the formula $$R^{iii}+SH)_c$$

wherein $c$ is an integer having a value of at least 2 and $R^{iii}$ is a polyvalent organic moiety of valence $c$. These polymercaptans will generally have a molecular weight in the approximate range of 94 to 20,000, preferably from 210 to 600.

In a presently preferred embodiment, the polymercaptan is an ester of a thiol-containing carboxylic acid of the formula $$R^{iv}+O_2C-R^v-SH)_d$$

wherein $d$ is an integer having a value of 2 to 4, $R^{iv}$ is a hydrocarbon radical having from 2 to 5 carbon atoms containing no reactive carbon-to-carbon unsaturation and $R^v$ is a divalent hydrocarbon radical having 1 to 2 carbon atoms containing no carbon-to-carbon unsaturation.

Examples of polymercaptans suitable for use in the present invention include ethane dithiol, hexamethylene dithiol, decamethylenedithiol, 2,4-tolylenedithiol, and the like, as well as polymeric polymercaptans. Examples of preferred polymercaptans include the esters of thioglycolic acid and $\alpha$- and $\beta$- mercaptopropionic acids, such as ethylene glycol bis(thioglycolate), ethylene glycol bis($\beta$-mercaptopropionate), trimethylolpropane tris(thioglycolate), trimethylolpropane tris($\alpha$-mercaptopropionate), pentaerythritol tetrakis(thioglycolate), and pentaerythritol tetrakis ($\beta$-mercaptopropionate).

These polymercaptans can be employed in any amount which results in the desired degree of cure and desired properties of the resultant cured composition. In general, desired properties are obtained when the amount of polymercaptan employed is in the range of 0.001 to 1 equivalent of mercaptan group per equivalent of carbon-to-carbon double bond of the olefinically unsaturated compound, preferably in the range of 0.5:1 to 1:1.

The photosensitizers which can be employed in the present invention are known in the art and include the aromatic ketones and halogenated hydrocarbons such as benzophenone, acetophenone, benzoin methyl ether, acenaphthene quinone, xanthen-9-one, fluoren-9-one, 1'-acetonaphthone, anthraquinone, 1-indanone, $\alpha$-tetralone, 1,3,5-triacetylbenzene, polychlorinated biphenyls, polychlorinated triphenyls, chlorinated rubbers, chlorinated waxes, chlorinated paraffins, mono-and polychlorobenzenes, mono- and polybromobenzenes, mono- and polychloroxylenes and the like and mixtures thereof.

The amount of photosensitizer used in the compositions of this invention is an amount which will bring about the desired cure. In general, this amount will be in the range of 0.01 to 10 weight percent, based on the total composition including the photosensitizer. Preferably, the amount used is in the range of 0.1 to 3 weight percent.

Optionally, the composition can contain a promoter which accelerates the rate of curing. Such promoters include the tertiary ethanolamines such as dimethyl ethanolamine, dipropyl ethanolamine, methyl diethanolamine, butyl diethanolamine, triethanolamine and the like and mixtures thereof. Methyl diethanolamine is particularly useful in the practice of this invention. The promoter, if used, is employed in a promoting amount, i.e., generally from 0.1 to 10 parts by weight per part by weight of photosensitizer, preferably from 0.5 to 2 parts per part of photosensitizer.

In another embodiment of the present invention, the previously described prepolymer prepared from the diisocyanate (A) and the olefinically unsaturated compound (B) wherein $m$ is 1, i.e., $$R^i-\underset{\underset{R^i}{|}}{C}-\underset{\underset{R^i}{|}}{C}-Y-(CR^i_2)_n-Z,$$

is compounded with the above-described photosensitizer and, optionally, the above-described promoter, and then cured.

The compositions to be cured in accordance with the present invention can, if desired, include such additives as antioxidants, dyes, fillers, pigments, anti-static agents, flame-retardant agents, thickeners, viscosity modifiers, plasticizers, tackifiers and the like. Such fillers include natural and synthetic resins, carbon blacks, glass fibers, wood flour, clay, silica, alumina, silicates, hydroxides, oxides, glass beads, talc and the like. These additives can be present in quantities up to about 500 parts or more per 100 parts by weight of the photocurable composition, preferably from about 0.0005 to about 300 parts by weight on the same basis.

The compounding of the components prior to curing can be carried out in several ways. For example, the components can be admixed and charged to an aerosol can, drum, tube or cartridge for subsequent use.

The curable compositions are cured by exposure to ultraviolet light, generally in the wavelength range of 2000 to 4000 Angstroms. Such light is available from sunlight and from many different commercial lamps including mercury vapor lamps, UV fluorescent lamps and the like.

The curable liquid compositions prior to curing can readily be pumped, poured, brushed, sprayed, doctored, or otherwise handled as desired. Following application, curing in place to a solid resin or elastomer can be effected either rapidly or slowly, as desired, by manipulation of the compounding ingredients and the method of curing.

Conditions of exposure to ultraviolet light under which the desired product is obtained are generally exposure of 0.1 second to 20 minutes at a temperature in the range of 0° to 100° C., preferably 1 second to 5 minutes at a temperature in the range of 20° to 40° C. It may sometimes be desirable to provide an inert atmosphere during the curing step.

The photocurable compositions of this invention are useful as coatings, both transparent and opaque, as printing inks and as adhesives.

The following examples illustrate the invention:

EXAMPLE I

A mixture containing 90 weight percent 5-methyl-1,9-nonanediamine, 9 weight percent 2,4-dimethyl-1,8-octanediamine and minor amounts of other isomers was prepared by catalytic hydrogenation (see U.S. Pat. Nos. 3,880,928 and 3,880,929) of the reaction product obtained from one mole of isobutylene and two moles of acrylonitrile (see U.S. Pat. No. 3,840,583).

This mixture of diamines was treated with concentrated hydrochloric acid to obtain the corresponding diamine dihydrochlorides. Treating of the thus-prepared amine salts with phosgene at 160 to 170° C. resulted in a mixture of diisocyanates which was distilled to provide a mixture consisting of 90 weight percent 5-methyl-1,9-nonanediisocyanate, 9 weight percent 2,4-dimethyl-1,8-octane-diisocyanate, and minor amounts of other isomers (this mixture of diisocyanates is hereinafter designated MNDI).

To 22.4 gm MNDI (0.1 moles) in a glass reactor was added 19.4 gm diallylamine (0.2 moles) in 2 gm increments. Following each incremental addition of diallylamine the reaction mixture was stirred and cooled to approximately room temperature (25° C.). The resulting prepolymer was a clear, viscous, pale yellow liquid.

A mixture consisting of 5.25 gm of the thus-prepared prepolymer, 6.1 gm of pentaerythritol tetrakis($\beta$-mercaptopropionate), and 0.1 gm of benzoin methylether was applied as a thin film to a glass plate and irradiated at room temperature with 100 watt Hanovia mercury vapor lamp for 3 minutes. The resulting coating on the glass was tough, flexible and glossy. A portion of the mixture in bulk form in a container likewise cured during 3 minutes exposure to the lamp.

EXAMPLE II

MNDI (22.4 gm, 0.1 mole) and dibutyltin dilaurate (0.13 gm) were mixed in a glass reactor. 2-Hydroxyethyl acrylate (23.2 gm, 0.2 mole) was added incrementally over a 15 minute period, with stirring and cooling of the reaction mixture to maintain it at approximately room temperature (25° C.). The reaction appeared to be complete within several minutes after completion of addition of 2-hydroxyethyl acrylate.

To 5.0 gm of the thus-prepared prepolymer was added a mixture containing 0.15 gm benzophenone and 0.23 gm methyldiethanolamine. Exposure of a thin film of this composition on a glass plate to a 100 watt Hanovia mercury vapor lamp for 30 seconds (1.5 inches from lamp) resulted in a hard, clear tough coating.

Reasonable variations and modifications, which will be apparent to those skilled in the art, can be made in this invention without departing from the spirit and scope thereof.

What is claimed is:

1. A photocurable composition consisting essentially of

A. A terminally unsaturated component formed by the reaction of
   (1) an aliphatic diisocyanate having from 9 to 32 carbon atoms and at least one alkyl side chain characterized by the formula

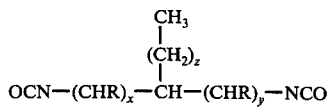

wherein each R is individually selected from the group consisting of hydrogen and alkyl having from 1 to 6 carbon atoms, x and y are, individually, integers having values in the range of 2 to 16, Z is an integer having a value in the range of 0 to 5 and the sum of (x+y) is in the range of 5 to 23; and
   (2) an unsaturated compound having a maximum of 12 carbon atoms per molecule characterized by the formula

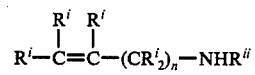

wherein each $R^i$ is individually selected from the group consisting of hydrogen and alkyl having from 1 to 6 carbon atoms, n is an integer having a value in the range of 1 to 6, and $R^{ii}$ is selected from the group consisting of $R^i$ and alkenyl having from 1 to 6 carbon atoms, wherein the reactant ratio of said diisocyanate to said unsaturated compound is about 1:2;

B. a cure-promoting amount of a polymercaptan having the formula

wherein c is at least 2 and $R^{iii}$ is a polyvalent organic moiety free from reactive carbon-to-carbon unsaturation; and C. a sensitizing amount of a photosensitizer.

2. The composition of claim 1 wherein said polymercaptan is characterized by the formula

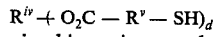

wherein d is an integer having a value of 2 to 4, $R^{iv}$ is a hydrocarbon radical having from 2 to 5 carbon atoms containing no reactive carbon-to-carbon unsaturation and $R^v$ is a divalent hydrocarbon radical having 1 to 2 carbon atoms containing no carbon-to-carbon unsaturation.

3. The composition of claim 1 wherein said polymercaptan is pentaerythritol tetrakis ($\beta$-mercaptopropionate).

4. The composition of claim 1 wherein said diisocyanate is an isomeric mixture containing 5-methyl-1,9-nonanediisocyanate in major amount, and said unsaturated compound is diallylamine.

5. The composition of claim 1 wherein said polymercaptan is present in an amount ranging from 0.001 to 1 equivalent of mercaptan group per equivalent of carbon-to-carbon unsaturation in said unsaturated compound.

6. The composition of claim 1 wherein said photosensitizer is present in an amount ranging from 0.01 to 10 weight percent.

7. A photocurable composition consisting essentially of

A. a terminally unsaturated component formed by the reaction of
   (1) an aliphatic diisocyanate having from 9 to 32 carbon atoms per molecule and at least one alkyl sidechain characterized by the formula

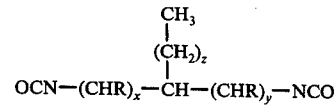

wherein each R is individually selected from the group consisting of hydrogen and alkyl having from 1 to 6 carbon atoms, x and y are, individually, integers having values in the range of 2 to 16, z is an integer having a value in the range of 0 to 5 and the sum of (x+y) is in the range of 5 to 23; and (2) an unsaturated compound having a maximum of 12 carbon atoms per molecule characterized by the formula $$R^j-\underset{\underset{R^i}{|}}{C}=\underset{\underset{R^i}{|}}{C}-(CR^i_2)_n-NHR^{ii}$$

wherein each $R^i$ is individually selected from the group consisting of hydrogen and alkyl having from 1 to 6 carbon atoms, $n$ is an integer having a value in the range of 1 to 6, Y is selected from the group consisting of $$-\underset{\underset{}{\overset{\overset{O}{\|}}{}}}{C}-O-,\ -\underset{\underset{}{\overset{\overset{O}{\|}}{}}}{C}-S-,\ \text{and}\ -\underset{\underset{R^{ii}}{|}}{\overset{\overset{O}{\|}}{C}}-N-,$$

$R^{ii}$ is selected from the group consisting of R and alkenyl having from 1 to 6 carbon atoms; wherein the reactant ratio of said diisocyanate to said unsaturated compound is about 1:2, and
  B. a sensitizing amount of a photosensitizer
  C. a cure-promoting amount of a polymercaptan having the formula $$R^{iii}\text{---}(SH)_c$$

wherein $c$ is at least 2 and $R^{iii}$ is a polyvalent organic moiety free from reactive carbon-to-carbon unsaturation.

8. The composition of claim 7 wherein said diisocyanate is an isomeric mixture containing 5-methyl-1,9-nonanediisocyanate in major amount, said unsaturated compound is 2-hydroxyethyl acrylate and said photosensitizer is benzophenone.

9. The composition of claim 7 wherein said diisocyanate molecule contains from 10 to 18 carbon atoms.

10. The composition of claim 7 wherein said diisocyanate molecule contains from 11 to 14 carbon atoms.

11. The composition of claim 7 wherein said polymercaptan is characterized by the formula $$R^{iv}\text{---}(O_2C-R'-SH)_d$$

wherein $d$ is an integer having a value of 2 to 4, $R^{iv}$ is a hydrocarbon radical having from 2 to 5 carbon atoms containing no reactive carbon-to-carbon unsaturation and $R^v$ is a divalent hydrocarbon radical having 1 to 2 carbon atoms containing no carbon-to-carbon unsaturation.

12. The composition of claim 11 wherein said polymercaptan is present in an amount ranging from 0.001 to 1 equivalent of mercaptan group per equivalent of carbon-to-carbon unsaturation in said unsaturated compound.

13. The composition of claim 7 wherein said photosensitizer is present in an amount ranging from 0.01 to 10 weight percent.

14. The composition of claim 7 wherein said diisocyanate is an isomeric mixture containing 5-methyl-1,9-nonanediisocyanate in major amount and said unsaturated compound is 2-hydroxyethyl acrylate.

* * * * *

UNITED STATES PATENT AND TRADEMARK OFFICE
CERTIFICATE OF CORRECTION

PATENT NO. : 4,119,510
DATED : October 10, 1978
INVENTOR(S) : Ralph P. Williams

It is certified that error appears in the above-identified patent and that said Letters Patent are hereby corrected as shown below:

Column 5, line 48, "A" second occurrence should be "a";

Column 6, line 33, delete "1" and insert therefor --- 2 ---;

Column 7, line 6, delete

"$R^i - C = C - (CR^i_2)_n - NHR^{ii}$" with $R^i, R^i$ above the two C's, and insert therefor --- $R^i - C = C - Y - (CR^i_2)_n - NHR^{ii}$ --- with $R^i, R^i$ above the two C's; and Column 8, line 31, delete "2-hydroxyethyl acrylate" and insert therefor --- diallylamine ---.

Signed and Sealed this

Fifteenth Day of May 1979

[SEAL]

Attest:

RUTH C. MASON
Attesting Officer

DONALD W. BANNER
Commissioner of Patents and Trademarks